United States Patent
Tuschy et al.

[11] Patent Number: 6,063,466
[45] Date of Patent: May 16, 2000

[54] COMPOSITE-PRELAMINATED CLOSURE TAPE SYSTEM

[75] Inventors: Joerg Otto Paul Tuschy, Bedburg; Axel Johannes Victor Dahm, Meerbusch, both of Germany

[73] Assignee: 3M Innovative Properties Company, St. Paul, Minn.

[21] Appl. No.: 08/894,099

[22] PCT Filed: Jan. 14, 1995

[86] PCT No.: PCT/EP95/00142

§ 371 Date: Nov. 10, 1997

§ 102(e) Date: Nov. 10, 1997

[87] PCT Pub. No.: WO96/21413

PCT Pub. Date: Jul. 18, 1996

[51] Int. Cl.[7] .................................................. A61F 13/62
[52] U.S. Cl. .................. 428/40.1; 428/41.8; 428/42.1; 428/42.2; 428/42.3; 428/43; 428/906; 604/389; 604/390; 604/391
[58] Field of Search .................................. 428/40.1, 906, 428/41.8, 42.1, 42.2, 42.3, 43; 604/389, 390, 391

[56] References Cited

U.S. PATENT DOCUMENTS

| | | | |
|---|---|---|---|
| 3,863,412 | 2/1975 | Bodycomb et al. | 52/483 |
| 4,617,022 | 10/1986 | Pigneul | 604/391 |
| 4,778,701 | 10/1988 | Pape et al. | 428/40 |
| 4,898,762 | 2/1990 | Brown | 428/152 |
| 5,019,073 | 5/1991 | Roessler et al. | 604/391 |
| 5,176,671 | 1/1993 | Roessler et al. | 604/391 |
| 5,549,591 | 8/1996 | Landvogt | 604/391 |

FOREIGN PATENT DOCUMENTS

| | | |
|---|---|---|
| 0 324 578 | 1/1989 | European Pat. Off. |
| 0 563 457 A1 | 4/1992 | European Pat. Off. |
| 0 563 458 A1 | 4/1992 | European Pat. Off. |
| 53-11127 | 11/1993 | Japan. |

*Primary Examiner*—Nasser Ahmad
*Attorney, Agent, or Firm*—Gary L. Griswold; Robert W. Sprague; William J. Bond

[57] ABSTRACT

A prelaminated composite tape in a stable roll from which a composite adhesive closure tape tab (20) for disposable articles can be cut, which comprises a support sheet (21) and a mechanical fastener (30), wherein the support sheet (21) has a fastening surface (22) with a bonding layer (24) and a back side surface (23) that is provided with means for increasing the static friction, whereby a first axial extending section (25) of the support sheet (21) has a patch (26) comprising a mechanical fastener (30) disposed on the bonding layer (24), and a second axial extending section (31) of the support sheet has an exposed bonding layer which is attached to the edge portion (14) of the disposable article (10) in the production process.

8 Claims, 4 Drawing Sheets

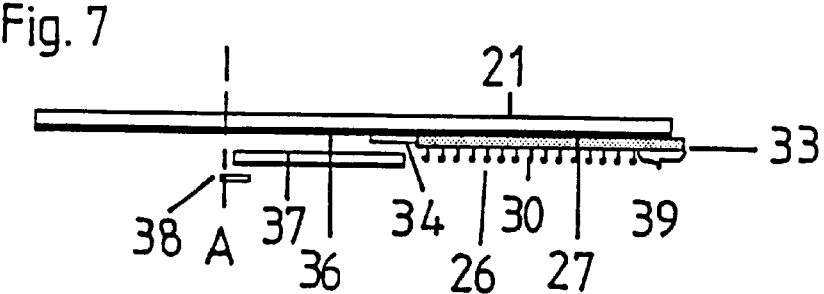
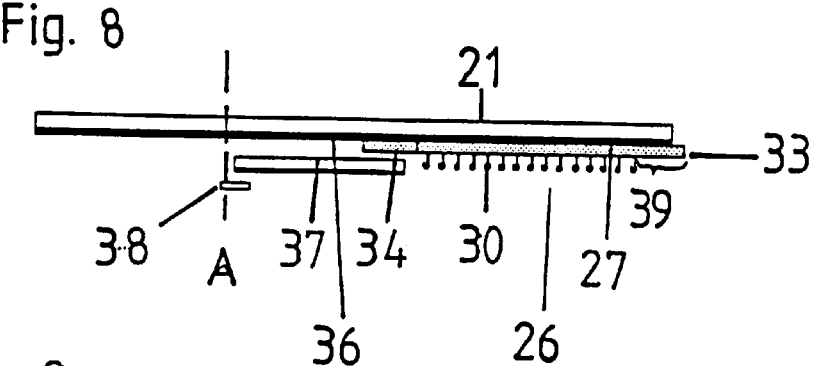
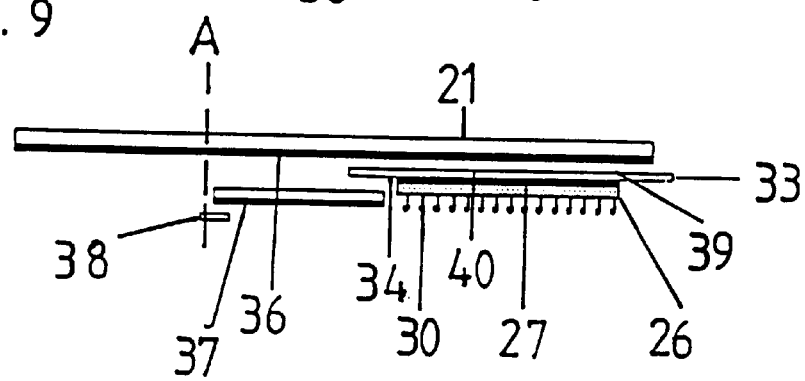
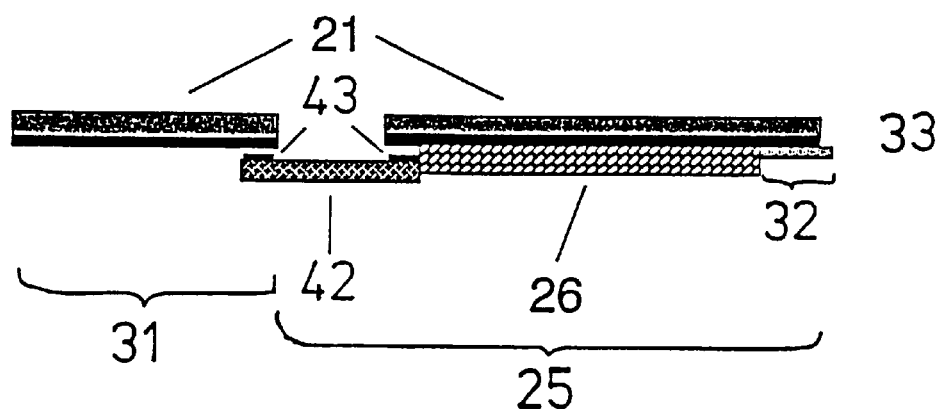

COMPOSITE-PRELAMINATED CLOSURE TAPE SYSTEM

FIELD OF THE INVENTION

The present invention relates to a roll of prelaminated strips from which a composite adhesive closure tape for disposable articles can be cut, wherein the closure tapes are provided in roll form to facilitate the use of such closure tapes in mechanised manufacturing methods, for example, in the manufacture of disposable articles, especially of diapers and disposable garments.

BACKGROUND OF THE INVENTION

A disposable diaper typically has a thin, flexible, stretchy, low density polyethylene back sheet film, an absorbent core on the inside of the backsheet film, and a porous top sheet overlying the core. Such a diaper is positioned at the crotch of the wearer, the two ends of the diaper extending, respectively toward the front and back. Adjacent edges of the diaper at each side are then either positioned adjacent to each other or overlapped, a strip of pressure-sensitive adhesive tape or mechanical fastener tape being adhered to the back sheet at the border adjacent each of the two edges, holding the diaper closed.

A desirable closure system which is used for disposable articles employs a mechanical fastener, comprising, for example, hook and loop fastening components. Mechanical fastening systems have the advantage that they may be repeatedly used for opening and refastening the disposable article. Closure systems which contain mechanical fasteners are described in U.S. Pat. Nos. 5,019,073 and 5,176,671 and in European patent applications 0324 578, 0 563 457 and 0 563 458. In practice, application of mechanical closures requires in-line lamination of all fastening and release components on the diaper manufacturing line. However, in-line lamination complicates the manufacturing process of the desired products, and sometimes causes problems for the manufacturers.

On the other hand, closure system fastening devices provided in roll form are generally adhesive tapes. Closure systems which contain adhesive closure tapes are described in U.S. Pat. No. 4,778,701 and in European patent application 0 324 578. Closure systems that comprise adhesive fastening tapes have the disadvantage that the adhesive may become contaminated with body fluids, powder and baby oil etc., and the adhesion of the tape may decrease. The closing or reclosing, respectively, of the diaper could become ineffective resulting in premature failure of the diaper.

Disposable articles, especially disposable diapers, must be made at high rates of speed in order to be manufactured economically. It is thus desirable for a manufacturer of diapers to mount a single roll of closure tape in the form of a prelaminate containing all necessary elements directly in the line of manufacture. The closure tape is applied to the diaper as a composite tape, with the width of the roll being substantially the same as the desired length of the diaper closure to be fabricated. The closure tape is servered at right angles to the edges of the composite tape roll at intervals corresponding to the width of the desired closure tape and adhered at an appropriate location along the border of one side of the diaper.

Such prelaminated composite rolls must dispense the closure tape in the form of a closure tab systematically and consistently so that it can reliably be employed in mechanised manufacturing systems, for example, in the manufacturing of diapers. To avoid problems in manufacturing, it is necessary that the roll of closure tape-be stable, i. e. that the roll can be unwound continuously and at a high speed so that a closure tab may be cut therefrom without telescoping of the roll. Closure tab rolls containing mechanical fastener components are not known, because of the different calipers of the layers forming the laminate backing, the roll obtained can be unstable and unsuitable for the in-line manufacturing process of disposable articles.

SUMMARY OF THE INVENTION

The present invention provides a prelaminated composite comprising a mechanical fastener component which may be wound into a stable roll from which a composite adhesive and mechanical fastener closure tape tab for disposable articles can be cut and which can be used in mechanized manufacturing processes. For example, the prelaminated composites are useful in the manufacture of diapers comprising an inexpensive fastening system which can securely close the article (garment) and allow a limited number of openings and closings of the fastener without seriously degrading fastener performance.

The present invention provides a prelaminated composite tape and mechanical fastener in a stable roll from which a composite adhesive closure tape tab for disposable articles can be cut, which comprises a support sheet and a mechanical fastener, wherein the support sheet has a fastening surface with a bonding layer and a back side surface which is provided with means for increasing the static friction, whereby a first axial extending section of the support sheet has a patch comprising a mechanical fastener disposed on the bonding layer, and a second axial extending section of the support sheet has an exposed bonding layer which is attached to the edge portion of the disposable article in the production process.

Accordingly, the subject matter of the present invention is a prelaminated composite closure tape dispensed from a stable roll to provide a closure tape tab with a mechanical fastener. Stable roll means that the roll of present invention can be unwound continuously and at a high speed so that a closure tab may be cut therefrom without telescoping of the roll. The manufacturer of diapers and other disposable garments may cut tabs in the appropriate length from the prelaminated roll during production. It is not necessary to laminate all fastening and tape components on the diaper manufacturing line, which sometimes results in unsuitable laminates. The use of the composite prelaminates of present invention provides advantages to the manufacturers of disposable diapers and garments. The inventive prelaminate containing the mechanical fastening system can be directly used in the manufacturing of the above mentioned articles without significant modification of the manufacturing line.

The closure tape obtained from the roll of the present invention can be securely attached to an edge of the product where the product shall be closed, for example, to the edge portions of a back sheet of a diaper, providing secure permanent attachment. The remaining portion of the closure tape includes the mechanical fastener that extends beyond the edge portion of the product to be attached to an adjacent sheet, for example, the opposite edge of a diaper.

DESCRIPTION OF THE DRAWINGS

FIGS. 6 to 9 are cross-sectional views of preferred embodiments of the closure tape tab of the invention FIG. 10 shows perspective view of a further embodiment of the closure tape tab of the invention

DETAILED DESCRIPTION

The details of the closure tape tab are best shown in FIGS. 2 to 12.

Figure 1:
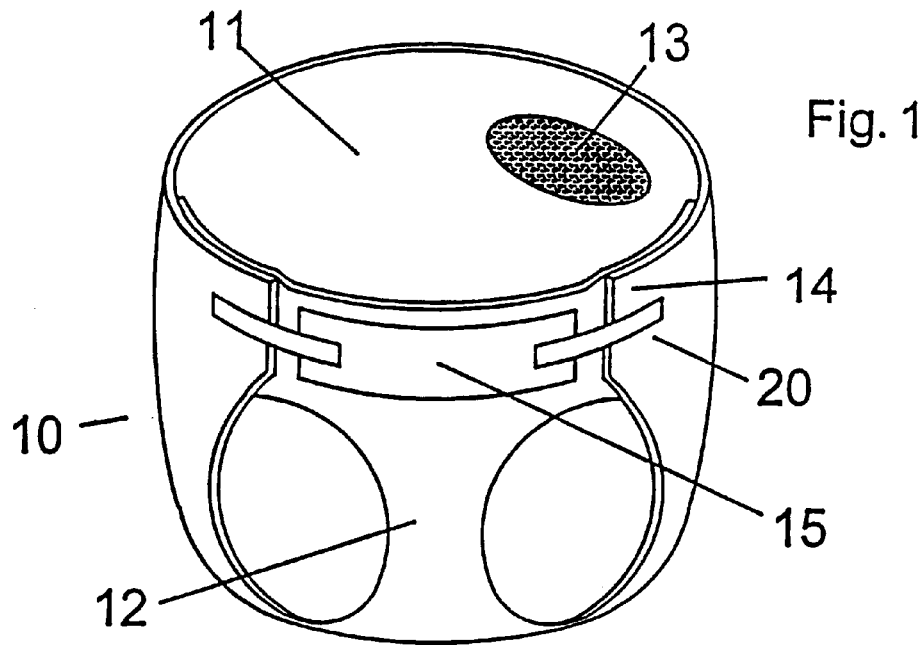
FIG. 1 is a perspective view of a diaper in a closed form
Figure 2:
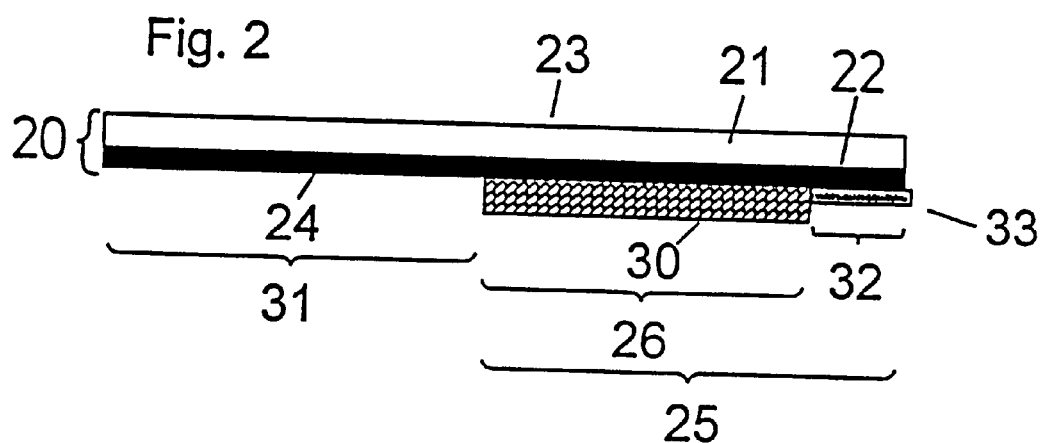
FIG. 2 is a schematic representation of a cross-section of the closure tape tab of the invention

As shown in FIG. 2, the closure tape tab composite 20 has a support sheet 21. The support sheet 21 may consist of any backing material to which bonding layers 24 may be applied. Suitable backing materials for support sheets 21 are for example cloth, kraft paper, cellophane film, nonwoven webs, polymeric films or other suitable materials or laminates. Polymeric films which may be used include polypropylene, poly(vinyl chloride), poly(ethylene terephthalate), and polyethylene film. Polypropylene film is presently preferred for diaper applications. Adhesive layer 24 is applied to the fastening surface 22 of support sheet 21. A low adhesion backsize (LAB) may be provided on the back side surface 23 of the support sheet. For example, the back side surface 23 can be coated with a release layer, such as a silicone layer. Before coating the release layer or the adhesive layer it might be desirable to provide corona treatment to one or both surfaces of the support sheet 21.

In order to obtain a stable roll the back side surface of the closure tape tab is provided with means for increasing the static friction of the back side surface to the mechanical fastener, which are in contact when the composite tape is rolled up. Such means can be various means which are useful to increase the static friction of the back side surface to the mechanical fastener and may be coated on the back side surface or can be inherent to the surface material. Preferably, the back side surface 23 of the support sheet 21 has a rough surface structure. The roughness of the back side surface 23 of polymeric sheets can be obtained by the film production process, e.g. casting or embossing, or by providing a coating on the surface 23. The production of such surface structures is well known to workers skilled in the art. The back side surface 23 preferably has a roughness Ra, measured as the average surface roughness with a laser scanner, of at least 1 $\mu$m, more preferably between 3.5 and 10 $\mu$m.

The support sheet 21 has a fastening surface 22 which is provided with the adhesive layer 24. To the first axial extending section 25 of the support sheet 21 a patch 26 comprising a mechanical fastener component 30 is disposed on the adhesive layer 24. The second axial extending section 31 of the support sheet 21 will be attached permanently to the edge portion 14 of the disposable diaper or garment 10 in the manufacturing process by the adhesive layer 24.

The permanent adhesive layer 24 is made of a material that should preferably have a peel strength that is sufficient to permanently attach the support sheet 21 to the outside surface of the disposable diaper or garment 10 and to permanently attach the patch 26 to the support sheet 21,even under load. That means, when the disposable diaper or garment 10 is used and when the closure tape 20 is opened and closed several times, the patch 26 should not be removed. The adhesive layer 24,which is provided on the fastening surface 22,may be any conventional adhesive layer, such as pressure-sensitive adhesives and non-pressure sensitive adhesives. Suitable pressure-sensitive adhesives include conventional rubber-based adhesives (also called rubber-resin adhesives) which have their tackiness modified by the inclusion of tackifying resins such as those described in U.S. Pat. No. 4,136,071, which describes adhesives comprising styrene-isoprene-styrene mixed block copolymers tackified with synthetic polyterpene resins.

Figure 3:
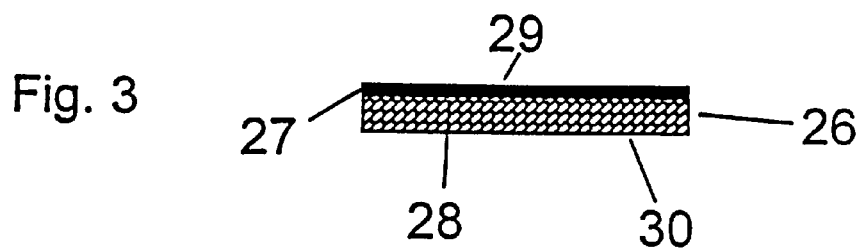
FIG. 3 is a schematic representation of the patch comprising the mechanical fastener patch

The general structure of the mechanical fastener patch 26 is shown in FIG. 3. It is essentially composed of a base sheet 27 with a first surface 29 which may be attached to the support sheet 21 by the adhesive layer 24 and a second surface 28 on which a mechanical fastener component 30 is provided. The base sheet 27 and the mechanical fastener component 30 may consist of the same or of different materials.

The mechanical fastener component 30 may be a part of any conventional mechanical fastener systems. A suitable fastening system is a hook and loop fastener comprising two interlocking materials, one of the components is a hook material and the other is a loop material. One component of the mechanical fastening system is part of the patch 26,and the other is on the target area 15 on the outside surface 12 of the disposable diaper or garment 10. For example, the target area 15 may be a strip which is attached to the outside surface 12 of the diaper 10 in such a manner that the size of the diaper or garment may be adjusted in accordance with the size of the user. The target area can comprise one or more stripes and could form the entire outside surface 12 of the diaper. Depending on the material of the outside surface 12,it may be possible that the fastening system will be releasably attached directly to the outside surface 12. For example, in case the mechanical fastener component 30 comprises a hook material, such hook material may be attached to a material being comprised of woven or non-woven fabric or any other suitable material which interlocks with a hook. The closure system comprises tape tab 20 with the mechanical fastener patch 26,together with target area 15.

Figure 4:
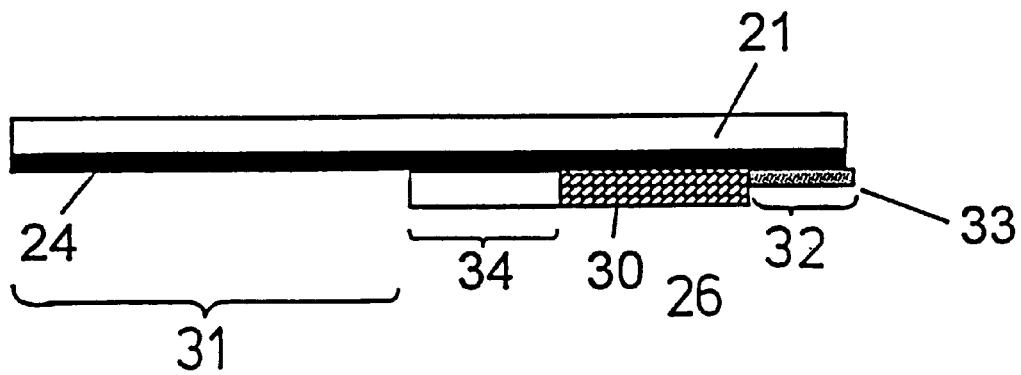
FIG. 4 is a cross-sectional view of preferred embodiments of the closure tape tab of the invention

In FIG. 4 an embodiment is shown wherein a spacer 34 is arranged beside the patch 26 on the first extending section 25 to provide a non-adhesive region. The spacer 34 may be used in order to make the disposable article more comfortable for the wearer. The spacer may be formed in various manners, such as providing a region of the support sheet 21 with no adhesive layer 24. Alternatively, a spacer material 34 such as a polymeric film material, paper or non-woven material may be attached to the adhesive layer 24. In further embodiments the area 34 can be rendered non-adhesive by designed contamination for example with grease, talcum or similar.

In order to increase the fastening strength of the closure tape it may be possible to use two or more different mechanical fastener components. For example, two different hook materials could be used, the hooks of one component oriented in a direction opposite to the orientation of the hooks of the second component.

Figure 5:
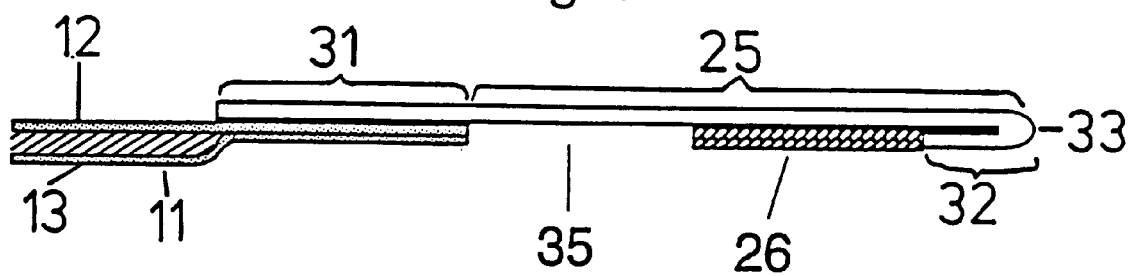
FIG. 5 is a cross-sectional view of the closure tape tab attached to one edge of a diaper
Figure 6:
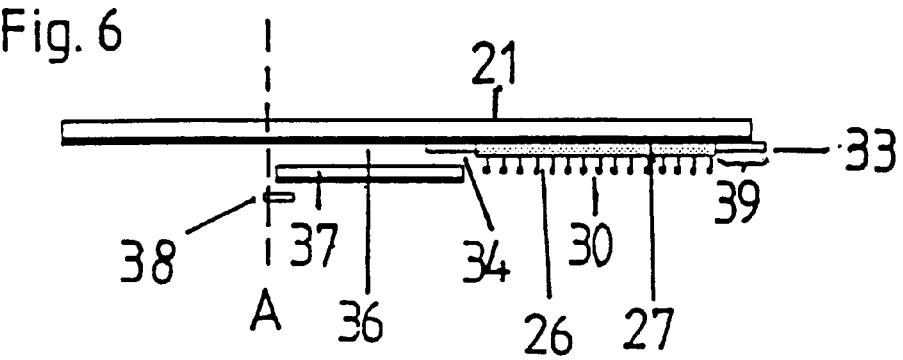

In the embodiment shown in FIG. 5, the support sheet 21 is not completely coated with adhesive layer 24 but is coated in regions in order to provide on the support sheet 21 a separating region 35 which is free from the adhesive layer 24 on the support sheet 21. This separating region is arranged on the first axial extending section 25. The embodiments shown in FIGS. 4 and 5 have the advantage that when the closure tape tab 20 is attached to the disposable diaper or garment, it may be easily folded into the form shown in FIG. 12.

Figure 12:
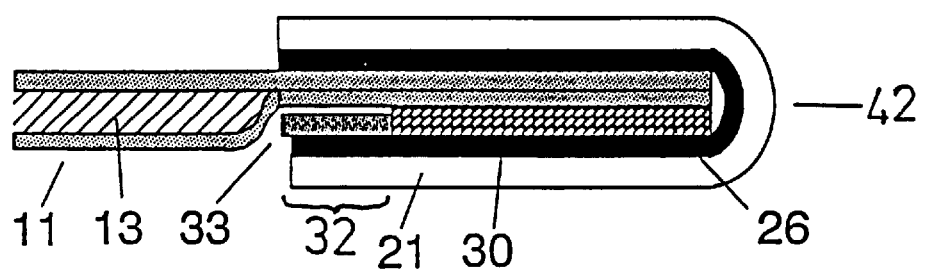
FIG. 12 is a cross-sectional view of the closure tape tab attached to one edge of a diaper, shown in the position during storage.

In FIGS. 6 to 9 embodiments are shown wherein the composite tape comprises an adhesive section 36 that facilitates the disposal of the disposable article 10 after use. Further, the closure tape tab 20 may be easily folded inside and maintained in the folded position during storage as shown in FIG. 12.

In the embodiments shown in FIGS. 6 to 9, an adhesive section 36 having uncovered adhesive layer 24 is formed between the patch 26 comprising the mechanical fastener component 30 and the edge portion 14. On the adhesive layer 24 a spacer 34 is disposed next to the patch 26. A release tape 37 is disposed on the adhesive section 36. In the embodiments shown in FIGS. 6 to 9, the release tape 37 covers the adhesive section 36 and extends from the edge portion 14 to the non-adhesive area 34. In case the release tape 37 covers also the non-adhesive area 34,it may be easily removed. The other end of the release tape is provided on the edge portion 14 of the disposable article. The release tape 37 protects the adhesive section 36 from contamination during storage and transport. As a release tape 37 any suitable release tape composed of three layers, i.e. of a support sheet comprising an adhesive layer and a non-adhesive layer, may be used. Persons skilled in the art can select a suitable release tape for the intended purpose. For transport and storage the closure tape is folded along the folding line A and the release tape 37 adheres to the inside surface 11. When opening the folded closure tape for use, the release tape 37 remains on the inside surface 11. During use, the open adhesive of the section 36 adheres to the target area 15 and supports the mechanical fastening system. After use, the disposable article 10 can be folded or rolled into a structure, such that the closure tape tab still extends outwardly from the rolled up disposable article 10. The adhesive section 36 is then secured to either the target area 15 or to the backsheet outside surface of the backsheet 12 so as to secure the disposable article 10 in its rolled up configuration such that it may be easily and conveniently disposed in a waste receptical.

For distribution of forces during use of the diaper, a center strip 38 is disposed on the line where the release tape 37 adjoins the edge 14 of the disposable article.

In the embodiment shown in FIG. 8, the spacer 34,i.e. non-adhesive area, is part of the patch 26. In this embodiment the extending sections 39 of the patch 26 do not contain mechanical fastener. The patch 26 is arranged on the support sheet 21 that the extending section 39 that is disposed on the free end 32 forms the finger tab 33 and the section next to the edge portion 14 of the disposable article is the spacer 34.

In the embodiment shown in FIG. 9, a non-adhesive film carrier 40 is provided between the adhesive layer 24 and the patch 26 on the support sheet 21. Between the film carrier 40 and the edge portion 14 is the adhesive section 36. The patch 26 is arranged on the film carrier 40 in such a manner that the distal ends of the film carrier 40 are not covered with the patch 26,thus forming the spacer 34 and the non-adhesive area 39,which is the finger tab 33.

In a further embodiment shown in FIG. 10 the closure tape 20 further includes an elastomeric sheet 42. The elastomeric sheet may be incorporated into the closure tape 20 for example in such a manner that the support sheet 21 is not a continuous strip but is divided in two parts which are connected by the elastomeric sheet 42. The adhesives used for attaching the elastomeric sheet to the support sheet, may be the same as the adhesive layer 24 described above. The elastomeric sheet 42 may also be attached to the support sheet 21 by adhesive glue lines 43. The elastomeric sheet 42 may be an elastomeric polyurethane film, or may be a synthetic or natural rubber. Elastomeric refers to a material which may be repeatedly stretched and returns to its original dimension after the stretching force is released. Polyurethane which is elastomeric is presently preferred. The elastomeric sheet 42 allows greater size adjustments for a disposable diaper or garment. The width of the elastomeric sheet 42 depends on the intended application and may be from 1 cm to 5 cm.

The first axial extending section 25 of the support sheet 21 may comprise at its free end a finger tab 33. The finger tab 33 is provided to allow easy removal of the extending section 25 from a surface from which it is attached to while in a pre-use state or to facilitate reopening. The finger tab 33 may be provided in the different embodiments shown in FIGS. 2 and 4 to 12. It is obvious for workers skilled in the art that the different embodiments of the finger tab may be combined with each embodiment of rolls of composite closure tape of the present invention.

In one possible embodiment of a finger tab, the material used to make a finger tab 33 will be a thin film, for example polypropylene film, non-woven, paper. The thin film is attached to the fastening surface 22 at the free end 32 of the first axial extending section 25 of the support sheet 21. In an alternative embodiment the free end 32 of the support sheet 21 is free from adhesive layer 24. In a third alternative embodiment the free end 32 of the support sheet 21 is completely coated with the adhesive layer 24 and then folded over. A finger tab of the third embodiment is, for example, shown in FIG. 5.

In the embodiment shown in FIG. 7, the patch 26 comprises an integrated finger lift. In such embodiment the base sheet 27 of the patch 26 has an extending section 39 without mechanical fastener and is arranged on the support sheet 21 that the extending section 39 without mechanical fastener is disposed on the free end 32 of the closure tape tab 20.

The width of the roll of composite closure tape the present invention also depends on the intended application. Usually the rolls which are used for closure tape tabs for disposable articles have a width of about 30 to about 100 mm and preferably from about 50 to about 70 mm. In order to provide a closure tape system which can be wound up to a stable roll, the first axial extending section 25 occupies 55 to 70%, and the second axial extending section 31 30 to 45%, of the width of the strip. In case a finger lift is used, the finger lift occupies 8 to 12%, the extending section 25 occupies 46 to 62%, and the second axial extending 31 occupies 30 to 42%, of the total width of the strip.

Figure 11:
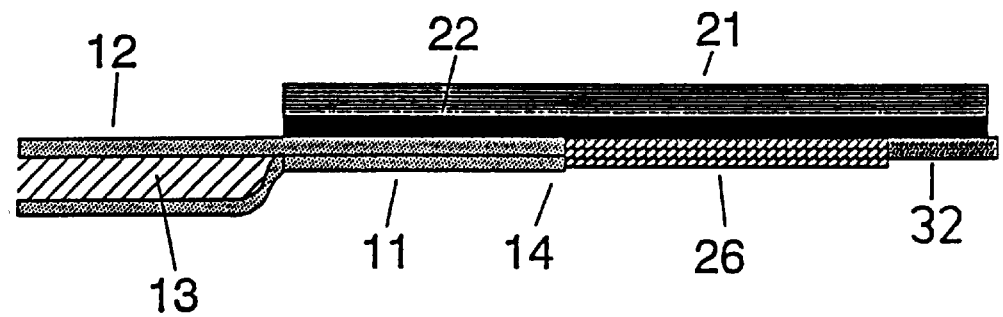
FIG. 11 is a cross-sectional view of the closure tape tab attached to one edge of a diaper, shown in the pre-use-position
Figure 13:
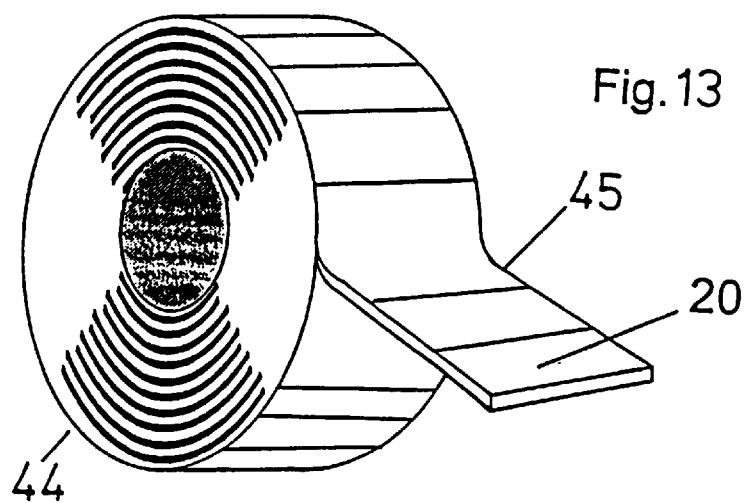
FIG. 13 is a perspective view of a roll of the closure tape

The closure tape tabs 20 of the invention can be cut from a stock roll 44. In use, a segment of a roll 44 of composite closure tape 45 is cut from the roll in a desired length; see FIG. 13, where the line shows where the tape is cut into tabs. Thereupon the fastening surface 22 of the support sheet 21 is secured to the outside surface 12 of the edge portion 14 of the diaper or garment 10 as shown in FIG. 11. The first axial extending section 25 is folded around the edge portion 14 and the closure tape is positioned in a folded form as shown in FIG. 12. Now, it is now in the pre-use position. The closure tape is folded so that it will not be unfolded prior to use or during manufacturing and storage. It is contemplated that a diaper would be sold to the consumer in this condition.

In use, a diaper 10 containing the composite closure tape tab 20 of the present invention is positioned around a wearer. To fit the diaper 10 the folded closure tape tab 20 is unfolded, for example the finger tab 33 is grasped and the closure tape tab 20 is then unfolded. The extending section 25 comprising the mechanical fastener component 30 is then secured to the outside surface 12, preferably to the target area 15. When the same process is followed on the other side of the wearer, the diaper is then secured in place. In case an elastomeric sheet 42 is incorporated into the closure tape, such sheet provides a flexible connection between the edge portions 14 of the diaper 10.

| List of references | |
|---|---|
| 10 | disposable article |
| 11 | inside surface |
| 12 | outside surface |
| 13 | absorbent core |
| 14 | edge portion |
| 15 | target area |
| 20 | closure tape tab |
| 21 | support sheet |
| 22 | fastening surface |
| 23 | back side surface |
| 24 | adhesive layer |
| 25 | first axial extending section |
| 26 | patch comprising mechanical fastener |
| 27 | base sheet of the patch |
| 28 | first surface of the base sheet 27 |
| 29 | second surface of the base sheet 27 |
| 30 | mechanical fastener component |
| 31 | second axial extending section |
| 32 | free end |
| 33 | finger tab |
| 34 | spacer |
| 35 | section free of adhesive material |
| 36 | adhesive section between the patch 26 and the distal end of second axial extending section 31 |
| 37 | release tape |
| 38 | center strip |
| 39 | extending section of the patch 26 without mechanical fastener |
| 40 | film carrier |
| 41 | folded closure system |

| -continued | |
|---|---|
| List of references | |
| 42 | elastomeric sheet |
| 43 | adhesive line |
| 44 | roll |
| 45 | closure tape |

What is claimed:

1. A prelaminated composite tape in a stable roll from which a composite adhesive closure tape tab for disposable articles can be cut, which comprises a polymeric support sheet and a mechanical fastener, wherein the polymeric support sheet has a fastening surface with a bonding layer and a back side surface that is provided with means for increasing the static friction comprising a roughened surface having an average surface roughness of between 3.5 and 10 $\mu$M, the support sheet having a first and second axial extending sections adjacent to one another whereby the first axial extending section of the support sheet has a patch comprising a mechanical fastener disposed on the bonding layer, and the second axial extending section of the support sheet has an exposed bonding layer.

2. A roll according to claim 1, wherein the free end of the first axial extending section comprises a finger tab.

3. A roll according to claim 1, wherein the patch comprises two or more mechanical fastener components.

4. A roll according to claim 1, wherein a part of the axial extending section of the support sheet adjacent to the edge portion of the disposable article does not contain an adhesive layer.

5. A roll according to claim 1, wherein a spacer is arranged beside the patch and adjoins the extending section that will be attached to the edge portion.

6. A roll according to claim 1, wherein the patch comprising the mechanical fastener does not adjoin to the edge portion and an adhesive section having uncovered adhesive layer is formed therebetween which is covered by a release tape.

7. A roll according to claim 6, wherein a non-adhesive film carrier is provided on the first axial extending section of the support sheet between the adhesive layer and the patch comprising the mechanical fastener component, whereby the distal ends of the film carrier are not covered with the patch thus forming a non-adhesive area and the spacer.

8. A roll according to claim 1, wherein the support sheet is divided in two parts which are connected by an elastomeric sheet.

\* \* \* \* \*